United States Patent [19]

Baumgartner

[11] Patent Number: 5,320,644

[45] Date of Patent: Jun. 14, 1994

[54] INTERVERTEBRAL DISK PROSTHESIS

[75] Inventor: Walter Baumgartner, Wil, Switzerland

[73] Assignee: Sulzer Brothers Limited, Winterthur, Switzerland

[21] Appl. No.: 922,711

[22] Filed: Jul. 30, 1992

[30] Foreign Application Priority Data

Aug. 30, 1991 [CH] Switzerland ............... 02552/91

[51] Int. Cl.[5] .............................................. A61F 2/44
[52] U.S. Cl. ........................................ 623/17; 606/61
[58] Field of Search ................ 623/17, 16, 18, 20; 606/61, 72

[56] References Cited

U.S. PATENT DOCUMENTS

| | | | |
|---|---|---|---|
| 3,707,731 | 1/1973 | Morgan | 623/49 |
| 3,951,366 | 4/1976 | Abernathy et al. | 248/560 |
| 4,309,777 | 1/1982 | Patil . | |
| 4,714,469 | 12/1987 | Kenna . | |
| 4,752,058 | 6/1988 | Weber | 248/615 |
| 4,759,769 | 7/1988 | Hedman et al. | 623/17 |
| 4,997,432 | 3/1991 | Keller | 623/17 |

FOREIGN PATENT DOCUMENTS

| | | | |
|---|---|---|---|
| 0346269 | 12/1989 | European Pat. Off. | 623/17 |
| 72.02248 | 9/1972 | France . | |
| 2124815 | 9/1972 | France . | |
| 0072709 | 10/1947 | Norway | 623/49 |
| 0727489 | 4/1980 | U.S.S.R. | 248/568 |

*Primary Examiner*—David Isabella
*Attorney, Agent, or Firm*—Townsend and Townsend Khourie and Crew

[57] ABSTRACT

An intervertebral disk prosthesis is described which with respect to its external dimensions imitates a natural intervertebral disk and connects two adjacent vertebrae to their upper and lower attachment surfaces. The intervertebral disk member is made of one piece from a strong, elastically deformable material and comprises parallel slits at a right angle to the connecting axis which partially overlap. In overlapping regions adjacent slits form parts of leaf springs for the transmission of forces from one attachment surface of the prosthesis to the other attachment surface.

15 Claims, 4 Drawing Sheets

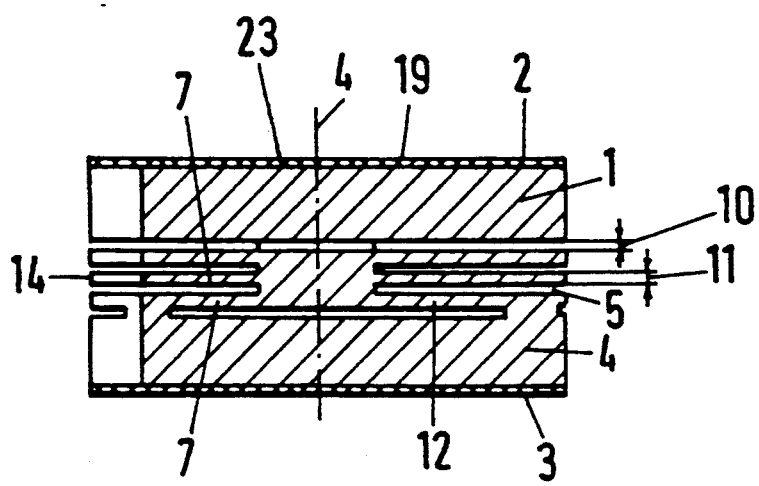
Fig. 2
Fig. 3
Fig. 1
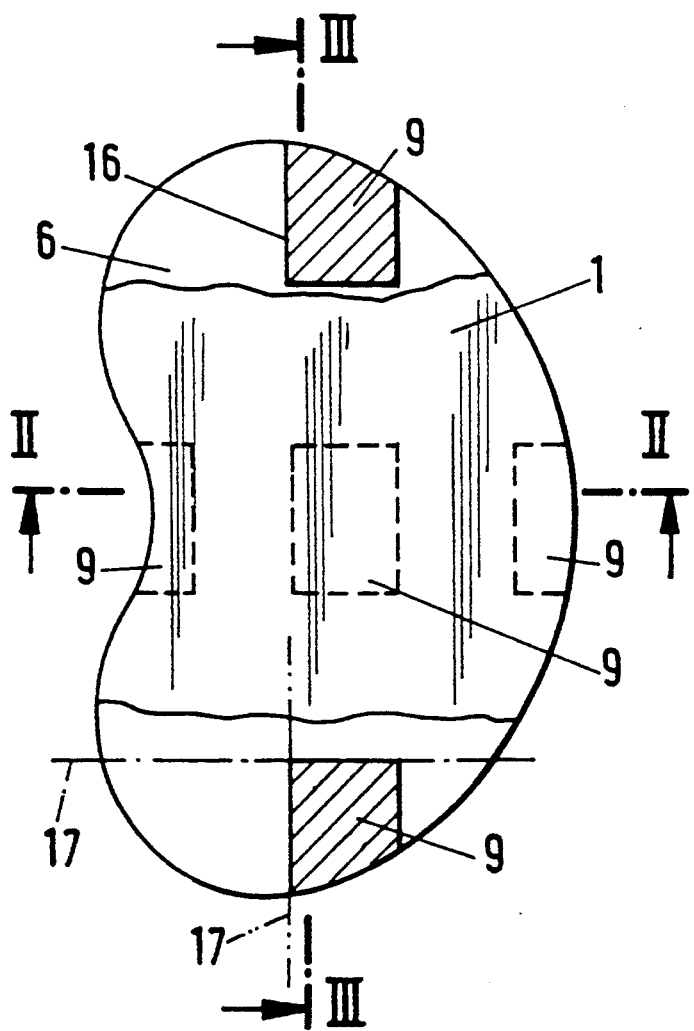
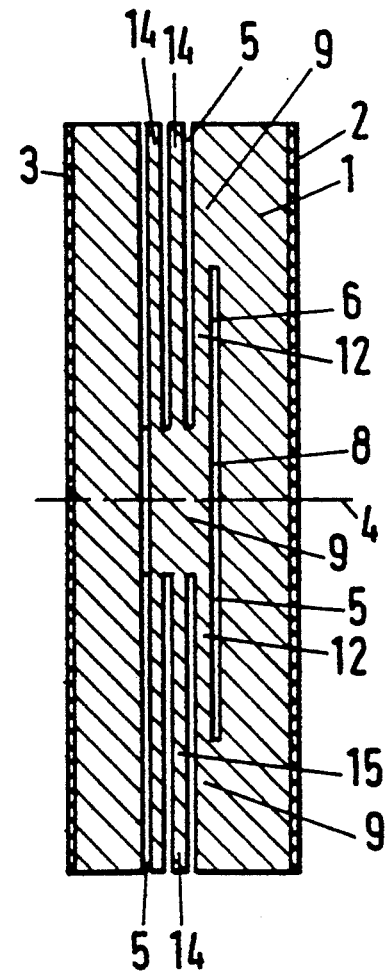

INTERVERTEBRAL DISK PROSTHESIS

BACKGROUND OF THE INVENTION

The invention relates to an intervertebral disk prosthesis, which with respect to its external dimensions conforms to those of a natural intervertebral disk and connects two adjacent vertebras. It includes an upper and lower attachment surface.

U.S. Pat. No. 4,309,777 discloses an intervertebral disk prosthesis consisting of a box with a lower and upper half, which can move relative to one another under the compression of inserted coil springs. This prosthesis has the disadvantage that the box edges sliding against one another can become jammed when subjected to bending loads, that abrasion is produced and that in the box there is an enclosed, relatively large empty volume which can become filled with body fluids.

SUMMARY OF THE INVENTION

The present invention remedies these problems. It is therefore an object of the present invention to create a simple intervertebral disk prosthesis which does not have the previously mentioned disadvantages. This object is achieved according to the present invention by constructing the intervertebral disk prosthesis in one piece from a strong, elastically deformable material. The prosthesis has parallel slits arranged at a right angle to its axis which partly overlap one another. Overlapping regions between adjacent slits form parts of leaf springs for the transmission of forces from one attachment surface to the other.

An advantage of the present invention is that the prosthesis is simple to manipulate. Further, under compression or bending loads it exhibits a non-linear spring characteristic which limits the amount of deformation.

BRIEF DESCRIPTION OF THE DRAWINGS

FIG. 1 is a plan view of an intervertebral disk prosthesis made according to the present invention and having leaf springs forming three fixation zones;

FIG. 2 is a side elevational view, in section, and is taken along line II—II of FIG. 1;

FIG. 3 is a front elevational view, in section, and is taken along line III—III of FIG. 1;

DETAILED DESCRIPTION OF THE PREFERRED EMBODIMENT

Figure 5:
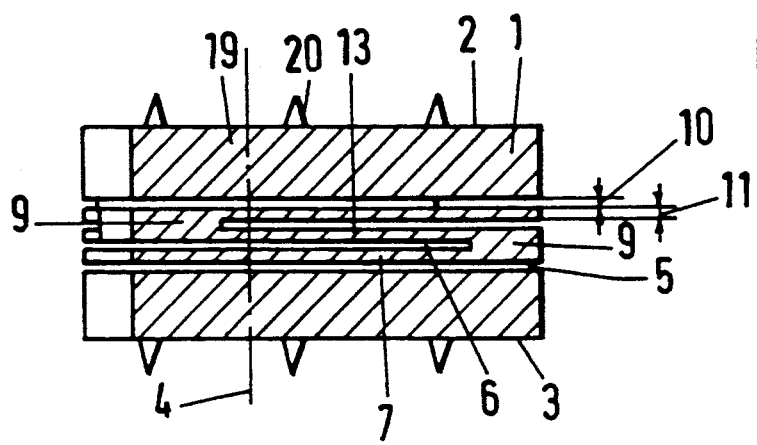
FIG. 5 is a side elevational view, in section, and is taken along line V—V of FIG. 4.

The FIGURES show an intervertebral disk prosthesis which with respect to its external dimensions imitates, i.e. are effectively the same as those of a natural intervertebral disk and which has upper and lower attachment surfaces for connection to adjacent vertebras. The intervertebral disk member is made of one piece from a strong, elastically deformable material and has partly overlapping parallel slits oriented at right angles to the connecting axis. Where adjacent slits overlap they form parts of leaf springs for the transmission of forces from one attachment surface to the other.

Referring to FIGS. 1, 2 and 3, an intervertebral disk member 1 has an upper boundary surface 2 and a lower boundary surface 3, each provided with a structured surface layer 19 which can be made from a lattice, for example. At a right angle to the vertical axis 4 of the prosthesis are slits 5 which extend into but never completely cut through the intervertebral disk member 1 so that it remains a single piece. The slits 5 are parallel to one another and partially overlap so that their boundary surfaces 8 form parts of leaf springs 7 in the overlapping regions 6 of adjacent slits 5. In regions of adjacent slits 5 where they do not overlap the spring action of the leaf springs 7 is interrupted by fixation zones 9 of solid prosthesis material. The forces acting on the intervertebral disk are transmitted from one leaf spring plane to the next leaf spring plane via fixation zones 9.

FIG. 3 illustrates that there are three fixation zones 9 in the uppermost leaf spring plane defined by leaf spring 12, two outer fixation zones 9 forming a transition to the upper part and a central fixation zone 9 forming a transition to the next lower leaf spring plane. There is only one central fixation zone 9 at leaf spring 15. FIG. 2 shows three fixation zones 9 in the lowest leaf spring plane. Leaf springs with three fixation zones are subject to bending and tension here, while the central leaf spring 15 generates an additional force under bending when only one side of its free end 14 bottoms out and prevents further movement when its free end 14 bottoms out on both sides. The free ends 14 of the other leaf springs act likewise as supplemental resistance and movement restrictors.

Figure 4:
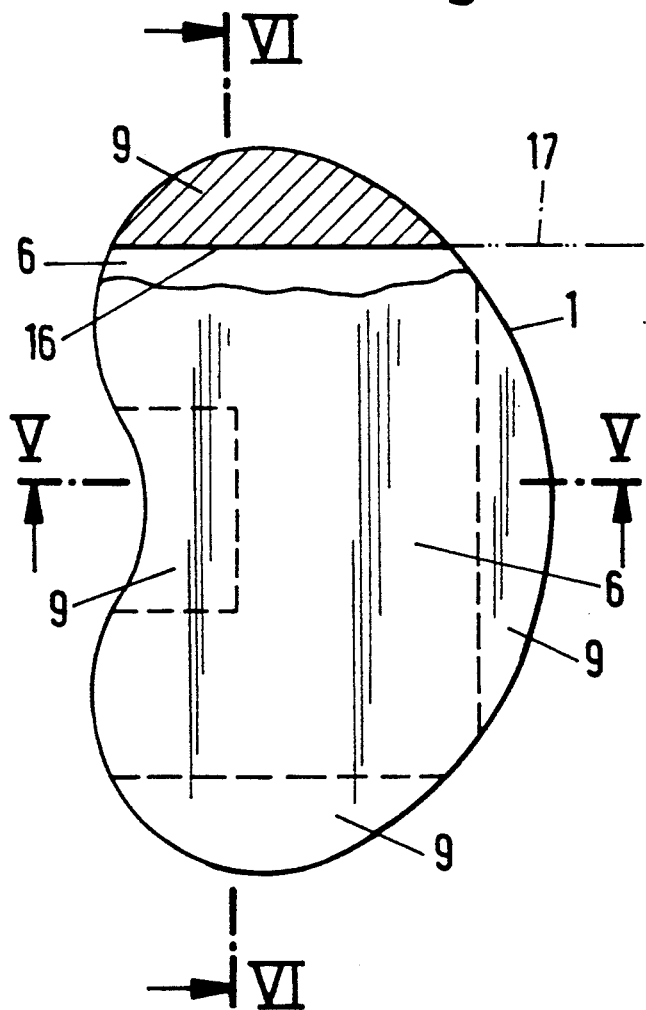
FIG. 4 is a plan view of an intervertebral disk prosthesis made according to another embodiment of the present invention which has leaf springs forming two fixation zones.
Figure 6:
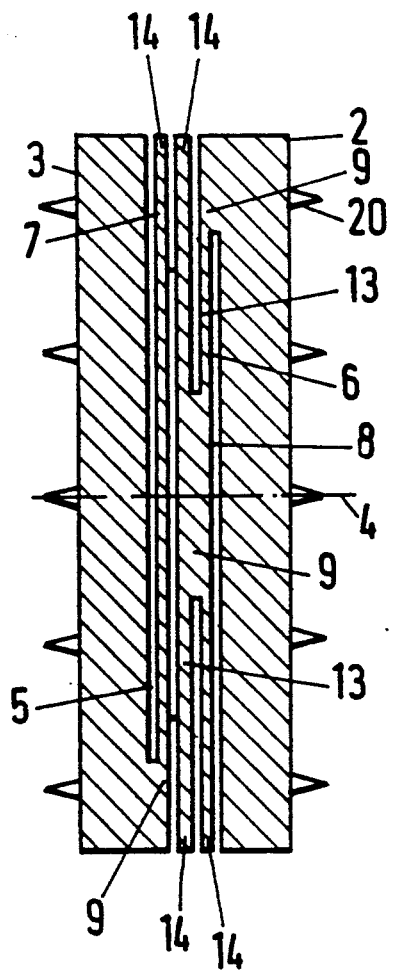
FIG. 6 is a front elevational view, in section, and is taken along line VI—VI of FIG. 4.

Referring to FIGS. 4, 5 and 6 the structured surface layers 19 are provided with teeth 20 and leaf springs 13 with two fixation zones 9. Each of the slits 5 is cut into disk member 1 from one side so that a generatrix or base 17 of one slit is at a right angle to the generatrix of an adjacent slit 5. Apart from the offset planes, the slits 5, cut into disc member 1 from medially opposite directions, are symmetrical with respect to one another so that no lateral flexion is produced between the upper attachment surface 2 and the lower attachment surface 3 when a centered compressive load is applied. Slit width 10 and leaf spring thickness 11 are selected so that when the compressive and/or bending loads exceed a predetermined level the slit width 10 is reduced to zero at some places on both sides of the leaf springs to form stops or limits against further movement before the elastic limit of the leaf springs is reached.

The manufacture of such intervertebral disk members depends on what material they are made of. It must be of adequate strength and elasticity. For metals such as titanium alloys, for example, the slits 5 can be formed by sawing or electrical discharge machining with a wire which produces a tangential generatrix 17 at the base 16 of the slit. Alternatively, the disk member can be constructed by laminating a plurality of leaf springs and interposing spacer blocks, with a thickness equal to the width of the slits, at the fixation zones 9. To assemble such a disk member, metallurgical connecting techniques can be used when it is made of metal. When the disk member is made of a plastic material, with or without fiber reinforcement, bonding agents exhibiting the desired high affinity to the plastic material are used. The structured surface 19 layer, which in the examples of FIGS. 1, 2 and 3 is a metal lattice 23, can be welded to a metal intervertebral disk member 1. If the intervertebral disk member 1 is made of plastic it can be partially embedded therein. Other fixation methods can of course be used.

Figure 8:
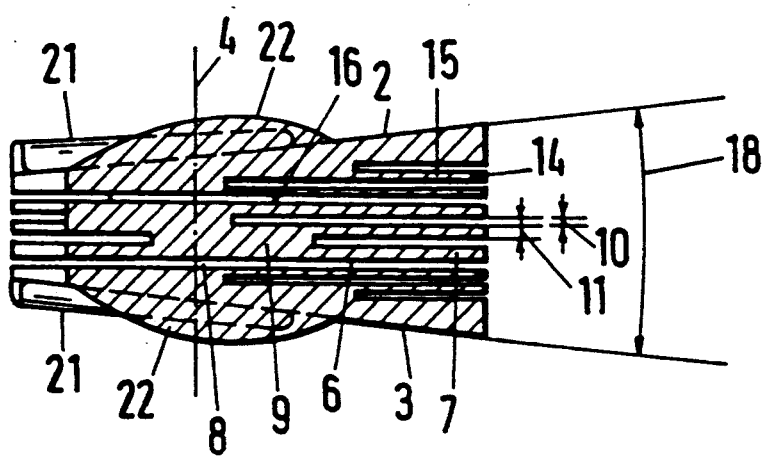
FIG. 8 is a side elevational view, in section, and is taken along line VIII—VIII of FIG. 7.
Figure 7:
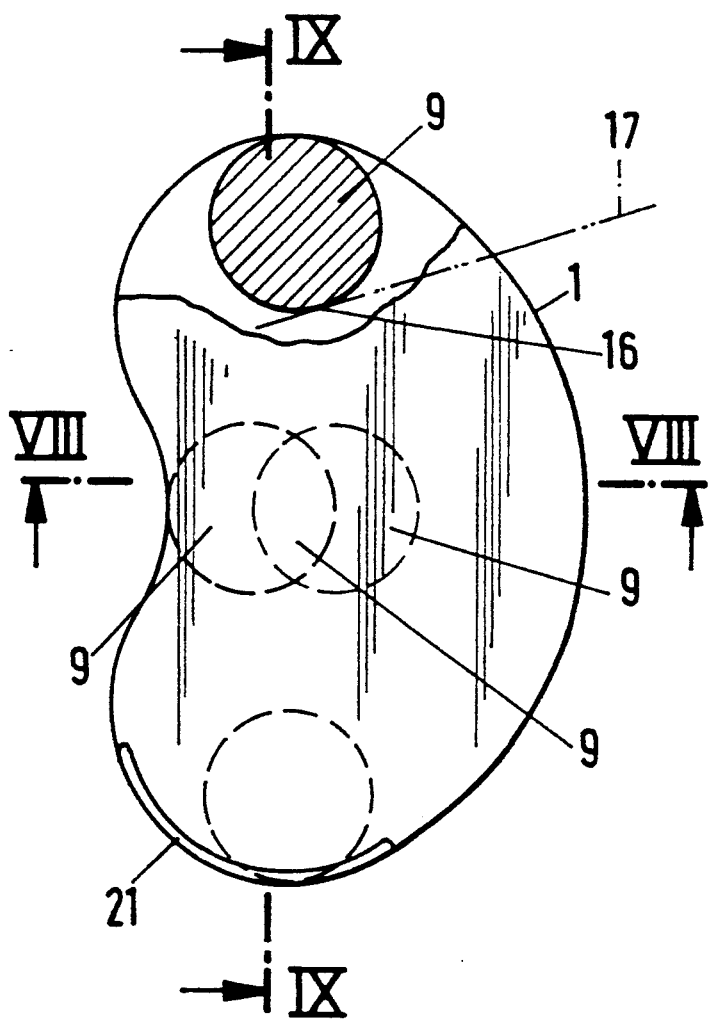
FIG. 7 is a plan view of an intervertebral disk prosthesis made according to a further embodiment of the present invention which has leaf springs forming two fixation zones and leaf springs forming one fixation zone.
Figure 9:
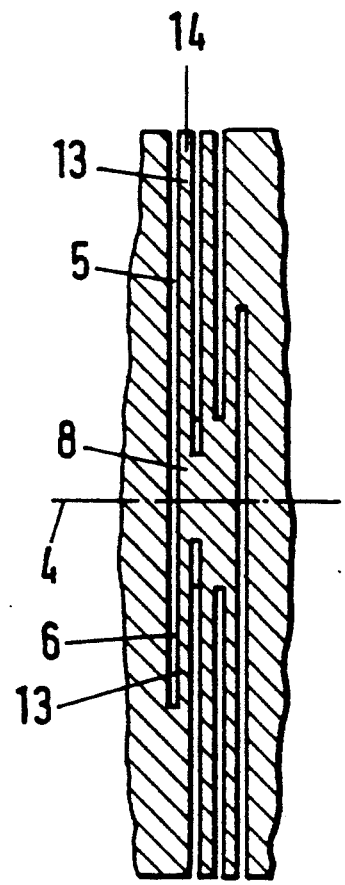
FIG. 9 is a front elevational view, in section, and is taken along line IX—IX of FIG. 7.

Referring to FIGS. 7, 8 and 9 the attachment surfaces 2, 3 are shown to converge in a wedge shape having a wedge angle 18 from the ventral to the dorsal side. The attachment surfaces 2, 3 are partially convex so that the disk member can be attached in surgically produced concave counter surfaces (not shown) in the adjacent vertebras. Partial collars 21 projecting towards the adjacent vertebra and preventing a slipping of the intervertebral disk prosthesis are shown in FIGS. 7 and 8. The fixation zones 9 have a circular cross section so that a tangential generatrix 17 only abuts the slit base 16 at one point and can be rotated around the central point of the circular fixation zone 9. The advantage of round fixation zones 9 lies in the fact that the load transmission into the spiral springs 7 does not depend on the direction. FIG. 8 shows leaf springs 15 which have only one distinct location defining the fixation zone 9. This is attained by cutting one of the adjacent slits from only one side. In this embodiment, when one spring is pressed against or contacts the free end 14 of another, additional resistance is produced until further movement is prevented when the boundary surfaces of adjacent springs at the opposite side of the slit contact each other.

Figure 11:
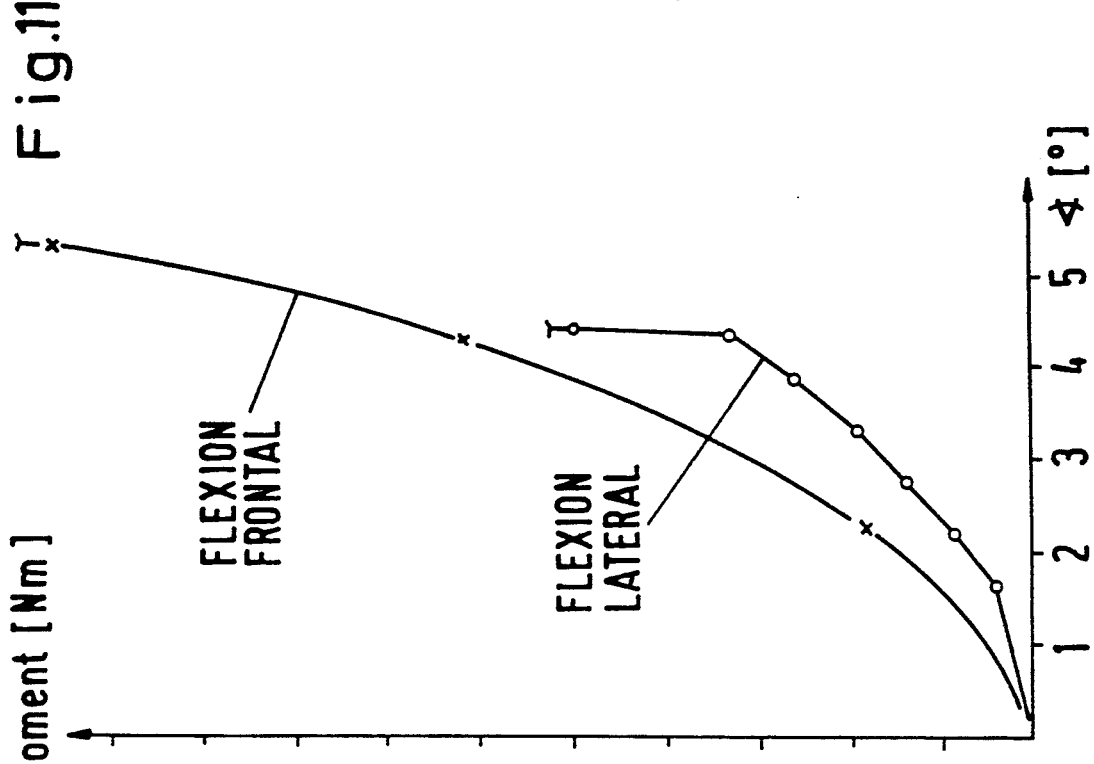
FIG. 11 is a diagram showing the non-linear spring characteristic of the bending moment as a function of angle of deflection when the intervertebral disk prosthesis is subjected to lateral and frontal flexion.
Figure 10:
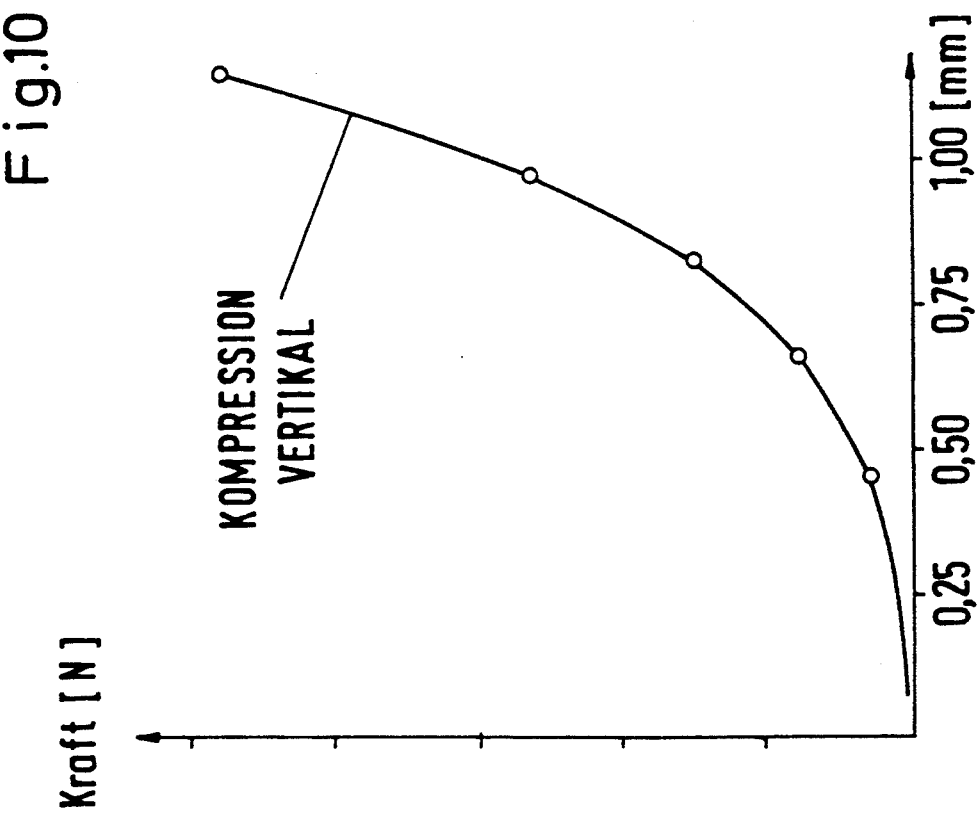
FIG. 10 is a diagram showing the non-linear spring characteristic of the compressive force as a function of deflection when the intervertebral disk is subjected to prosthesis vertical compression.

Intervertebral disk members 1 may be constructed to exhibit non-linear characteristics under compression and bending if, in the course of the deformation of leaf springs, additional leaf springs become engaged or additional fixation points are produced as a result of deformation. Typical measurement results for compression and for flexion of an intervertebral disk prosthesis are illustrated in the diagrams of FIGS. 10 and 11. FIG. 10 shows the relationship between a compressive force acting along axis 4 in newtons and the resulting deformation of the intervertebral disk member in millimeters. FIG. 11 shows the bending moment in newton meters for different angles of deflection in degrees for bending in both the frontal direction and the lateral direction.

What is claimed is:

1. An implantable intervertebral disk member for use as a replacement of a natural intervertebral disk between two adjacent vertebras of a spinal cord of a patient, the disk member comprising a one-piece body shaped and dimensioned to substantially conform to that of the natural disk it is to replace and forming spaced-apart, upper and lower attachment surfaces for connection of the disk member to the adjacent vertebras, the body being made of a solid, elastically deformable material and having a unitary construction, the body including a plurality of parallel slits oriented at a right angle to an axis of the disk member, the slits extending into the body to a sufficient depth so that proximate slits partially overlap and thereby define overlapping regions forming portions of leaf springs adapted to transmit bending forces, weight loads and shear loads applied to the disk member by the adjacent vertebras when the disk member is implanted in a patient's spinal cord.

2. An implantable intervertebral disk member according to claim 1 wherein the material of the body, a thickness of the leaf springs, and a width of the slits is selected so that opposing surfaces of adjacent spring leafs separated by a slit contact each other, and thereby prevent further relative deflection of the adjacent leaf springs, under a force which is less than a force stressing the material of the body beyond its elastic limit.

3. An implantable intervertebral disk according to claim 2 wherein the body includes at least first and second slits extending into the body and defining a leaf spring between them having first and second boundary surfaces opposite and spaced by the slits from contact surfaces defined by a remainder of the body, the slits being formed so that a resistance of the body against further deformation under an axial force applied to it increases when one of said first or second boundary surface of the leaf spring engages one of the opposing contact surfaces and so that further deflection of the body under said axial force is prevented when both boundary surfaces of the leaf spring come into contact with the opposing contact surfaces.

4. An implantable intervertebral disk member according to claim 3 wherein the body is constructed of metal.

5. An implantable intervertebral disk member according to claim 4 wherein the body is constructed of a homogeneous material and the slits extend to a predetermined depth into the body and terminate in a linear slit base at an interior of the body.

6. An implantable intervertebral disk member according to claim 3 wherein the slits defined a plurality of leaf springs spaced apart in the direction of the axis of the disk member and lying each in a plane perpendicular to the axis of the disk member, and including at least three inflexible regions defined by the body connecting the leaf spring in at least one plane perpendicular to the axis of the disk member with a remainder of the body, wherein forces acting on the implantable intervertebral disk member are transmitted from one plane perpendicular to the axis of the disk member to another plane perpendicular to the axis of the disk member through the inflexible regions.

7. An implantable intervertebral disk member according to claim 3 wherein the slits define a plurality of leaf springs spaced apart in the direction of the axis of the disk member and lying each in a plane perpendicular to the axis of the disk member, and including at least two inflexible regions defined by the body connecting the leaf spring in at least one plane perpendicular to the axis of the disk member with a remainder of the body, wherein forces acting on the implantable intervertebral disk member are transmitted from one plane perpendicular to the axis of the disk member to another plane perpendicular to the axis of the disk member through the inflexible regions.

8. An implantable intervertebral disk member according to claim 3 wherein the slits define a plurality of leaf springs spaced apart in the direction of the axis of the disk member and lying each in a plane perpendicular to the axis of the disk member, and including at lest one inflexible region defined by the body connecting the leaf spring in at least one plane perpendicular to the axis of the disk member with a remainder of the body, wherein forces acting on the implantable intervertebral disk member are transmitted from one plane perpendicular to the axis of the disk member to another plane perpendicular to the axis of the disk member through the inflexible regions.

9. An implantable intervertebral disk member according to claim 4 wherein the implantable intervertebral disk member has a ventral side and a dorsal side, and wherein the upper and lower attachment surfaces converge from the ventral side to the dorsal side and together define a wedge.

10. An implantable intervertebral disk member according to claim 9 including a material layer applied to the attachment surfaces forming a structured surface for facilitating the attachment of the disk member to opposing surfaces of the adjacent vertebras.

11. An implantable intervertebral disk member according to claim 9 wherein the attachment surfaces include a portion having a convex shape for engaging a correspondingly concave surface formed in the adjacent vertebras between which the disk member is to be implanted.

12. An implantable intervertebral disk member according to claim 4 including a collar formed by the body along a portion of a periphery of the body and projecting in the direction of the axis of the disk member past at least one attachment surface.

13. An implantable intervertebral disk member for implantation in a spinal cord of a patient between two adjacent vertebras of the spinal cord and as a replacement of a natural intervertebral disk of the spinal cord, the disk member comprising a unitary body with an attachment surface for attachment to the adjacent vertebras, made of a high strength, elastically deformable material, a plurality of narrow slits extending from a periphery of the body into and terminating in slit base at an interior of the body to thereby define a plurality of leaf springs spaced apart by the slits in an axial direction of the disk member, the leaf springs being secured to each other at inflexible regions defined by the body and proximate the slit bases, the inflexible regions between proximate leaf springs being offset with respect to each other so that the application of a force acting in an axial direction results in deflections of the attachment surfaces, whereby, upon the implantation of the disk member in the spinal cord of a patient, the disk member maintains the adjacent vertebras spaced apart and permits relative movement of the adjacent vertebras in a manner approximating the manner in which the natural intervertebral disk it replaces permits such relative movements.

14. An implantable intervertebral disk member for use as a replacement of a natural intervertebral disk between two adjacent vertebras of a spinal cord of a patient, the disk member comprising a one-piece body shaped substantially the same as the natural intervertebral disk it is to replace and forming spaced-apart, upper and lower attachment surfaces for connection of the disk member to the adjacent vertebras, the body being made of a solid, elastically deformable material and having a unitary construction, the body including a plurality of parallel slits oriented at a right angle to an axis of the disk member, the slits extending into the body to a sufficient depth so that proximate slits partially overlap and thereby define overlapping regions forming portions of leaf springs adapted to transmit forces applied to the disk member by the adjacent vertebras when the disk member is implanted in a patient's spinal cord, whereby the application of a force to the attachment surfaces causes a controlled deflection of the leaf springs and a corresponding deflection of the attachment surfaces so that the disk member deflects and thereby acts similar to the natural intervertebral disk which it replaces when the disk member is implanted between the adjacent vertebras.

15. An implantable intervertebral disk prosthesis comprising a body shaped and dimensioned to correspond to the shape and dimension of a natural intervertebral disk which it replaces, for placement between two adjacent vertebras, the body having an upper attachment surface being made in one piece from an elastically deformable material, and including parallel slits at a right angle to an axis of the prosthesis which partially overlap so that in an overlapping region a leaf spring is formed to transmit forces from the upper attachment surface to the lower attachment surface, the attachment surfaces converging in a wedge shape from a ventral side to a dorsal side of the intervertebral disk prosthesis.

* * * * *